United States Patent
Souza et al.

(10) Patent No.: US 8,013,176 B2
(45) Date of Patent: Sep. 6, 2011

(54) PARICALCITOL PURIFICATION

(75) Inventors: Fabio Eduardo Silva e Souza, Mississauga (CA); Ming Pan, Mississauga (CA); Kathleen Da Silva Turcot, Toronto (CA)

(73) Assignee: Alphora Research Inc., Mississauga (CA)

( * ) Notice: Subject to any disclaimer, the term of this patent is extended or adjusted under 35 U.S.C. 154(b) by 0 days.

(21) Appl. No.: 12/543,600

(22) Filed: Aug. 19, 2009

(65) Prior Publication Data
US 2010/0063307 A1    Mar. 11, 2010

Related U.S. Application Data

(63) Continuation-in-part of application No. 12/431,068, filed on Apr. 28, 2009, now Pat. No. 7,795,459.

(30) Foreign Application Priority Data

Sep. 11, 2008  (CA) .................................... 2639477
Jul. 24, 2009  (CA) .................................... 2673905

(51) Int. Cl.
*C07C 401/00*    (2006.01)
*C07C 35/21*     (2006.01)

(52) U.S. Cl. ........................................ 552/653; 568/819
(58) Field of Classification Search ........................ None
See application file for complete search history.

(56) References Cited

U.S. PATENT DOCUMENTS

| 5,086,191 | A | 2/1992 | DeLuca et al. | |
| 5,281,731 | A | 1/1994 | DeLuca et al. | |
| 6,903,083 | B2 * | 6/2005 | Knutson et al. | 514/167 |
| 2005/0148558 | A1 * | 7/2005 | Knutson et al. | 514/167 |
| 2007/0093458 | A1 | 4/2007 | Schwartz et al. | |

FOREIGN PATENT DOCUMENTS

WO    WO2007011951    1/2007

* cited by examiner

*Primary Examiner* — Brian J Davis
(74) *Attorney, Agent, or Firm* — McMillan LLP

(57) ABSTRACT

Paricalcitol, a synthetic vitamin D analog, is purified to a purity greater than 99.7% by crystallization from solution in isopropyl acetate solvent, followed by filtration and vacuum drying. Isopropyl acetate appears to be unique among commonly available and pharmaceutically acceptable solvents in its ability to precipitate paricalcitol in this high purity, essentially free of isomers thereof. In addition, paricalcitol of purity of at least 99.9% has been shown to have exceptional storage stability.

4 Claims, No Drawings

PARICALCITOL PURIFICATION

FIELD OF THE INVENTION

This invention relates to the vitamin D analog paricalcitol, and more particularly to methods for its purification.

BACKGROUND OF THE INVENTION AND PRIOR ART

Paricalcitol (1), also known as 1α,25-dihydroxy-19-nor-vitamin $D_2$, is a synthetically manufactured vitamin D analog developed for the treatment of secondary hyperparathyroidism associated with chronic renal failure.

The known synthetic route to paricalcitol utilizes 25-hydroxyvitamin D2 (2) as the key starting material, but this compound is quite costly and has very limited commercial availability. As a result, alternative syntheses to compound 2 and its derivatives have been developed, mostly based on the functionalization of the Inhoffen-Lythgoe diol (3).

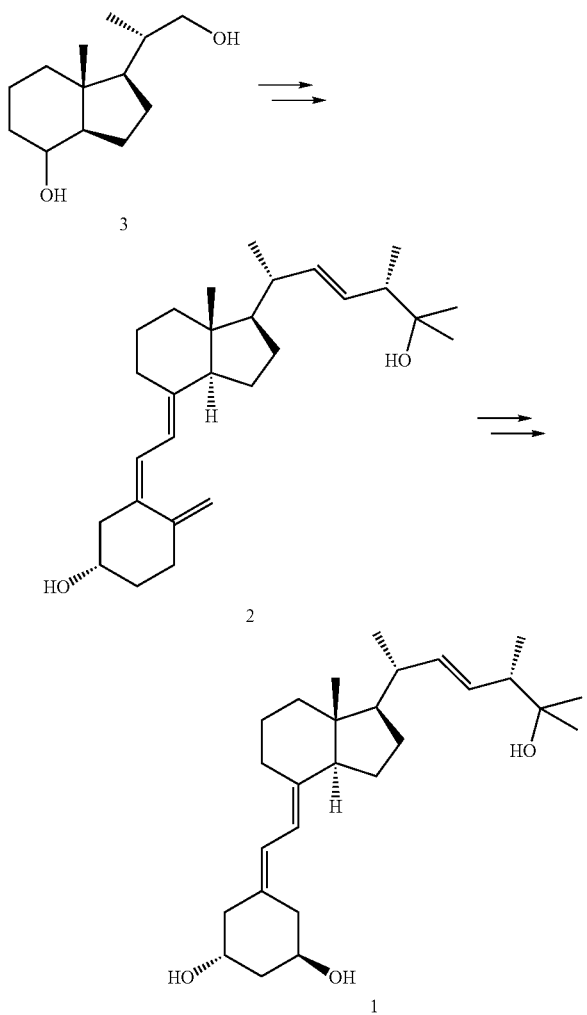

Such approaches involve a significant number of complex chemical transformations, with formation of several impurities, many of which carry through to the final active pharmaceutical ingredient (API). Of particular concern is the C20 epimer of paricalcitol, so similar in structure that even the HPLC analytical method listed in the United States Pharmacopeia fails to resolve both compounds. High purity of the final compound is important not only from the viewpoint of pharmaceutical safety and effectiveness of the final compound, but also from the product stability aspect.

U.S. Pat. Nos. 5,281,731 and 5,086,191 describe the purification of paricalcitol by preparative HPLC, but the cost and labor associated with this method make it undesirable for large scale manufacturing. More recently, published patent application US 2007/0093458 discloses crystallization procedures for the purification of paricalcitol. However, the examples given produce material of insufficient purity and/or in relatively low yields. Furthermore, the procedures described are volumetrically inefficient and many of them also require precise control of solvent ratios, volumes and temperatures.

SUMMARY OF THE INVENTION

The present invention, according to one aspect, provides a simple process for the purification of crude paricalcitol into API quality material. It comprises crystallization of solid impure paricalcitol from solution in isopropyl acetate. Recovery of paricalcitol is usually greater than 80%. Purity of the isolated material is usually greater than 99.7%, and the amount of C20 epimer is reduced by at least 60%. Particularly impure samples can be purified by successive such crystallizations.

Another aspect of the present invention is based on the discovery of a purity-stability relationship for paricalcitol. It has been found that paricalcitol purified to 99.9% and above, has a storage stability that significantly exceeds that of less pure (but still pharmaceutically acceptable) forms of paricalcitol. Thus a second aspect of the present invention is stabilized paricalcitol having a purity of at least 99.9% and exhibiting no reduction in purity in accelerated stability tests characterized by storage under an air headspace for 1 month at 40±2° C. and 75%±2% relative humidity.

DESCRIPTION OF THE PREFERRED EMBODIMENTS

Isopropyl acetate appears to be unique among industrially acceptable solvents in its ability to dissolve paricalcitol at temperatures close to the boiling point of the solvent and selectively precipitate paricalcitol on cooling, in this high degree of purity, to the substantially complete exclusion of other isomers. Moreover, this solvent is suitably volatile, relatively inexpensive, safe and non-toxic, with a high degree of pharmaceutical industry acceptability.

In the process, solid impure paricalcitol is preferably dissolved in isopropyl acetate at reflux temperatures, and crystallization is achieved by cooling the solution to room temperature or below. A solvent to substrate ratio of about 40:1 to 60:1, preferably about 50:1 (v/w) is suitably used. The solid impure paricalcitol is preferably obtained by trituration of crude paricalcitol with tert-butyl methyl ether followed by filtration. MTBE is a particularly desirable medium for the trituration, on account of its acceptable volatility (leaving little residue) and its industry acceptability.

The paricalcitol product of preferred embodiments of the present invention, in other accelerated stability studies, exhibits no reduction in purity after storage for 5 months under an argon headspace at 40±2° C. and 75±2% relative humidity. In the test protocol of the International Conference on Harmonization (ICH), these products according to the invention show no reduction in purity after storage for 6 months at −20±5° C. under argon headspace, and no reduction in purity after storage for 6 months at 5±3° C. under argon headspace.

Specific Description of the Most Preferred Embodiment

Example 1

Trituration of Crude Paricalcitol

Crude Paricalcitol (3.84 g, theoretical Paricalcitol content 3.11 g) was triturated with MTBE (75 mL) at room temperature for 30 minutes, collected by filtration and washed with additional MTBE (20 mL). After drying under high vacuum at room temperature for 24 h, Paricalcitol was isolated as a white solid (2.67 g, 85% yield).

Example 2

Crystallization

Paricalcitol prepared as in Example 1 (5.34 g) was suspended in isopropyl acetate (240 mL) and refluxed until all solids had dissolved. The resulting solution was filtered hot, and precipitation was immediately observed. The suspension was allowed to cool down to ambient temperature over a 2 h period, after which it was cooled to 4° C. (refrigerator) for 1.5 h. The solids were collected by filtration and dried under high vacuum at room temperature for 18 h to give Paricalcitol as a crystalline white powder (4.59 g, 86% recovery), with 99.87% purity, as determined by HPLC.

Example 3

Stability Studies

Paricalcitol samples prepared according to the procedures described in the previous Examples and having a purity of 99.9% as determined by HPLC, were placed under accelerated storage conditions. Samples "a" were placed in glass bottles and sealed in a Marvel seal bag under an argon head space, all air having been removed. These were stored at a temperature of 40±2° C. and relative humidity of 75±2%. Samples "b" were similarly packaged and sealed under argon headspace, but stored at 25±2° C. and 60±5% relative humidity. Samples "c" were similarly packaged and sealed under argon headspace, but stored at 5±3° C. Samples "e", comparative standards, were similarly packaged and sealed under argon headspace, but stored at −20±5° C.

Samples "d" and "f" were placed in glass bottles, but without a marvel seal bag, and stored under air headspace −20±5° C. (samples "d") and 40±2° C. and relative humidity of 75±2% (samples "f").

Samples stored at elevated or reduced temperatures were brought to room temperature just prior to sample preparation.

Purity determinations were conducted by High Performance Liquid Chromatography (HPLC), using a Waters Sunfire C18 HPLC Column, 250 by 4.6 mm, with a quaternary or binary HPLC pump, a variable wavelength or photo diode array UV/visible detector set to 252 nm, and an autosampler. Water (degassed) and acetonitrile (degassed) were used as the mobile phase. The column temperature was 25° C., the flow rate 2.0 mL/min with an injection volume of 100 μL and a run time of 60 minutes.

Initially, every sample showed a purity of 99.9%. After 1 month of storage, all samples still showed a purity of 99.9%. Samples "c" and "e" were tested again after 2 months storage, and still showed a purity of 99.9%. Samples "a", "c", "d" and "e" were tested again after 5 months storage, and again showed a purity of 99.9%, no change. Samples "b" after 5 months storage showed a slight reduction in purity, to 99.8%. Samples "f" were not tested after 5 months storage.

What is claimed is:

1. Stabilized paricalcitol having a purity of at least 99.9% and exhibiting no reduction in purity in accelerated stability tests characterized by storage under an air headspace for 1 month at 40±2° C. and 75%±2% relative humidity.

2. Stabilized paricalcitol according to claim 1 further exhibiting no reduction in purity after storage for 5 months under an argon headspace at 40±2° C. and 75±2% relative humidity.

3. Stabilized paricalcitol according to claim 2 further exhibiting, according to ICH test protocol, no reduction in purity after storage for 6 months at −20±5° C. under argon headspace and no reduction in purity after storage for 6 months at 5±3° C. under argon headspace.

4. Stabilized paricalcitol according to claim 1 purified by a process which comprises:
   i. dissolving a solid impure paricalcitol composition in isopropyl acetate solvent;
   ii. and recovering purified paricalcitol from the solution by crystallization.

* * * * *